US005753445A

United States Patent [19]
Fillit et al.

[11] Patent Number: 5,753,445
[45] Date of Patent: May 19, 1998

[54] TEST FOR THE DETECTION OF ANTI-HEPARIN ANTIBODIES

[75] Inventors: Howard M. Fillit, Tenafly, N.J.; Peter C. Harpel, New York, N.Y.

[73] Assignee: The Mount Sinai Medical Center of the City University of New York, New York, N.Y.

[21] Appl. No.: 233,390

[22] Filed: Apr. 26, 1994

[51] Int. Cl.$^6$ ................................................. G01N 33/53
[52] U.S. Cl. ........................... 435/7.1; 435/7.2; 435/7.92; 435/7.94; 435/13; 436/531; 436/513; 436/506; 436/821
[58] Field of Search ..................... 530/388.25; 435/7.1, 435/7.2, 7.92, 7.94, 13, 971, 329, 344.1, 345; 436/531, 501, 503, 821, 513, 506

[56] References Cited

U.S. PATENT DOCUMENTS

| 4,202,872 | 5/1980 | Collen | 424/1 |
|---|---|---|---|
| 4,859,581 | 8/1989 | Nicolson et al. | 435/4 |
| 4,985,542 | 1/1991 | Fillit et al. | 530/395 |
| 5,466,582 | 11/1995 | Amiral | 435/7.9 |

OTHER PUBLICATIONS

P. Faaber, et al., "Cross-reactivity of Human and Murine Anti–DNA Antibodies with Heparan Sulfate," *The American Society for Clinical Investigation*, 77:1824–1830 (1986).

R. M. Termaat et al., "Anti–heparan Sulphate Reactivity in Sera from Patients with Systemic Lupus Erythematosus with Renal or Non–renal Manifestations," *Clin. Exp. Immunol.*, 82:268–274 (1990).

S. Aotsuka, et al., "Analysis of Negatively Charged Dye-binding Antibodies Reactive with Double–stranded DNA and Heparan Sulfate in Serum from Patients with Rheumatic Disease," *Clin. Exp. Immunol.*, 73:436–442 (1988).

T. Sasaki, et al., "Heterogeneity of Immune Complex-derived Anti–DNA Antibodies Associated with Lupus Nephritis," *Kidney International*, 39:746–753 (1991).

Charnley, L. W., et al., "Inhibition of Heparin/Antithrombin III Cofactor Activity by Anticardiolipin Antibodies: A Mechanism for Thrombosis," *Thrombosis Research*, 71:103–111 (1993), Jul. 15, 1993.

Shibata, S. et al., "Autoantibodies to Vascular Heparan Sulfate Proteoglycan in Systematic Lupus Erythematosus React with Endothelial Cells and Inhibit the Formation of Thrombin–Antithrombin III Complexes", *Clin. Exp. Immun. Immunopath.*, 70:114–123 (1994).

Shibata, S. et al., "Monoclonal Antibodies to Heparan Sulfate Inhibit the Formation of Thrombin–Antithrombin III Complexes", *Clin. Immunol. Immunopathol.*, 67:264 (1993).

Fillit, H. et al., "Sera from Patients with Poststreptococcol Glomerulonephritis Contain Antibodies to Glomerular Heparan Sulfate Proteoglycan," *J. Exp. Med.*, 161:277 (1985).

Fillit, H. et al., "Antibodies to Vascular Heparan Sulfate Proteoglycan in Patients with Systemic Lupus Erythematosus," *Autoimmunity*, 9:159 (1991).

Fillit, H. et al., "Autoantibodies to the Protein Core of Vascular Basement Membrane Heparan Sulfate Proteoglycan in Systemic Lupus Erythematosus," *Autoimmunity*, 14:243 (1993).

Harpel, P.C., et al., "Novel Immunoenzyme Assays for Thrombin–Antithrombin III and Thrombin–$\alpha_{-2}$–Macroglobulin Complexes in Plasma," *Ann. N.Y. Acad. Sci.*, 485:184 (1986).

Termaat, R.M., et al., "Anti–heparan Sulfate Reactivity in Sera from Patients with Systemic Lupus Erythematosus with Renal or Non–Renal Manifestations," *Clin. Exp. Immunol.*, 82:268 (1990).

Aotsuka, S. et al., "Analysis of Negatively Charged Dye–Binding Antibodies Reactive with Double–Stranded DNA and Heparan Sulfate in Serum from Patients with Rheumatic Diseases," *Clin. Exp. Immunol.*, 73:436 (1988).

van den Born, J., et al., "Production and Characterization of a Monoclonal Antibody Against Human Glomerular Heparan Sulfate," *Lab. Invest.*, 65:287 (1991).

Shibata, S., et al., "Autoantibodies to Heparin From Patients With Antiphospholipid Antibody Syndrome Inhibit Formation of Antithrombin III–Thrombin Complexes," *Blood*, 83:2532–2540 (1994).

Shastry et al., "Antibodies to N–Acetyl Glucosamine and Heparin in Acute and Remission Phases of Rheumatic Fever," *J. Clin. Lab. Immunol.* (1991):35, 65–69.

*Primary Examiner*—Carol A. Spiegel
*Attorney, Agent, or Firm*—Hamilton, Brook, Smith & Reynolds, P.C.

[57] ABSTRACT

This invention pertains to a method of detecting, in a sample obtained from an individual, anti-heparin antibodies which inhibit the formation of the heparin accelerated antithrombin III-thrombin complex. In the present method, the presence of such anti-heparin antibodies are detected directly (by detecting the presence of anti-heparin antibodies themselves) or indirectly (by detecting the presence or formation of the heparin accelerated antithrombin III-thrombin complex). In one embodiment of the present method, antibodies which react with or interfere with the heparin pentasaccharide which binds antithrombin III in such a manner that binding to antithrombin III is inhibited are detected. In a specific embodiment of the present method, the anti-heparin antibody detected is one which reacts with or interferes with the disaccharide UA-2S/GlcNs-6 present in residues IV and V of the heparin pentasaccharide that binds antithrombin III.

20 Claims, No Drawings

TEST FOR THE DETECTION OF ANTI-HEPARIN ANTIBODIES

GOVERNMENT FUNDING

This invention was made, in whole or in part, with United States Government support under GCO Project #89-068 awarded by the National Institutes of Health. The United States Government has certain rights in the invention.

BACKGROUND OF THE INVENTION

Vascular heparan sulfate proteoglycans (vHSPG) play an important role in the structure and function of the vasculature, including endothelial cell adhesion and basement membrane structure, vascular permeability barrier integrity, normal hemostasis, lipolysis, and vascular repair. (David, G., Adv. Exp. Med. Biol. 313:69 (1992)). Vascular heparan sulfate (vHS), a glycosaminoglycan (GAG), constitutes the majority of the anionic sites of the capillary permeability barrier, binds to platelet factor 4, and plays a role in the function of growth factors, cytokines, and other molecules that are important in the cellular and extracellular matrix functions of the vasculature. (Jackson, R. L. et al., Physiol. Rev. 71:481 (1991)) HS plays an important role in the delicate balance of coagulation through a variety of mechanisms that ultimately, at least in part, inhibit thrombin activity. Endothelial vHSPG binds antithrombin III; and heparin cofactor II and markedly enhances the inhibition of thrombin. (Mertens, G. et al., J. Biol. Chem. 267:20435 (1992); van Deerlin, V., et al., Semin. Thromb. Hemost. 18:341 (1992)) HS contains the pentasaccharide also found in heparin which is involved in normal anti-coagulation. However, the number of pentasaccharide epitopes in HS is small compared to heparin.

Antibody directed against HS GAG has been shown in both humans and animals. (Faaber P., et al., J. Clin. Invest. 77:1824 (1986); Termaat, R. M., et al., Clin. Exp. Immunol. 82:268 (1990); Fillit, H., Lahita R., Autoimmunity 9:159 (1991); Kure, S., Yoshie O., J. Immunol. 137:3900 (1986); Shibata S., et al., Clin. Immunol. Immunopathol. 67:264 (1993)). Studies of the fine specificity of antibodies directed against heparin sulfate have shown that regions of HS containing highly sulfated residues are immunodominant sites of HS/heparin GAG. (van Deerlin, V., et al., Semin. Thromb. Hemost. 18:341 (1992); Shibata S., et al., Clin. Immunol. Immunopathol. 67:264 (1993)). Monoclonal antibodies (MoAbs) to heparin (Kure, S., Yoshie O., J. Immunol. 137:3900 (1986); Strauss, A. H., et al., Anal. Biochem. 201:1 (1992)) and HS (van den Born, J. et al., Lab. Invest. 65:287 (1991); Shibata S., et al., Clin. Immunol. Immunopathol. 67:264 (1993)) have been produced that are immunologically specific. Several studies have shown humoral autoimmunity to HS in patients with systemic lupus erythematosus (SLE). (Faaber P., et al., J. Clin. Invest. 77:1824 (1986); Termaat, R. M., et al., Clin. Exp. Immunol. 82:268 (1990); Fillit, H., Lahita R., Autoimmunity 9:159 (1991); Pillit H., et al., Autoimmunity 14:243 (1993); Shibata S., et al., Clin. Immunol. Immunopathol. 67:264 (1993)). Autoantibodies to HS correlate with disease manifestations in SLE. (Sasaki, T., et al., Kidney Int. 39:746 (1991); Termaat, R. M., et al., Clin. Exp. Immunol. 82:268 (1990); Aotsuka, S. et al., Clin. Exp. Immunol. 73:436 (1988)). Furthermore, IgG autoantibodies to HS are present in the eluates from glomeruli of patients with renal disease. (Faaber P., et al., J. Clin. Invest. 77:1824 (1986); Sasaki, T., et al., Kidney Int. 39:746 (1991)) showing the presence of these anti-HS antibodies at the site of vascular injury. In animal models, sera and eluates from the kidneys of autoimmune mice (Faaber P., et al., J. Clin Invest 77:1824 (1986)) contain antibodies to HS, and MoAbs to HS induce marked proteinuria. (van den Born, J., et al., Kidney Int 41:115 (1992)). Immunization with HS results in a coagulopathy with a prolonged partial thromboplastin time. (Bona, C. A., Autoimmunity 10:169 (1991)). These findings fulfill the criteria necessary to show that an autoantibody is pathogenic. (Bona, C. A., Autoimmunity 10:169 (1991)).

Serum assays for detection of antibodies against heparin have generally proven unreliable. Numerous molecules in serum may bind heparin and form macromolecular complexes that may interfere with the detection of specific antibodies to heparin by increasing nonspecific interactions. In addition, the presence of endogenous circulating heparin in serum and heparin sulphate epitopes that may be exposed along the entire vasculature confound assays for circulating antibodies to heparin. It would be highly advantageous to be able to precisely detect antibodies which bind heparin in an individual.

SUMMARY OF THE INVENTION

This invention pertains to a method of detecting, in a sample obtained from an individual, anti-heparin antibodies which inhibit the formation of the heparin accelerated antithrombin III-thrombin complex. In the present method, the presence of such anti-heparin antibodies is detected directly (by detecting the presence of anti-heparin antibodies themselves) or indirectly (by detecting the presence or formation of the heparin accelerated antithrombin III-thrombin complex). In one embodiment of the present method, antibodies which react with or interfere with the heparin pentasaccharide which binds antithrombin III in such a manner that binding to antithrombin III is inhibited are detected. In a specific embodiment of the present method, the anti-heparin antibody detected is one which reacts with or interferes with the disaccharide UA-2S/GlcNs-6S present in residues IV and V of the heparin pentasaccharide that binds antithrombin III.

In one embodiment, anti-heparin antibodies are detected indirectly by determining the extent to which the complex is formed. Formation of the complex to a lesser extent in the presence of the sample than in its absence is indicative of the presence of anti-heparin antibodies. In another embodiment, anti-heparin antibodies are detected directly. In this embodiment, anti-heparin antibodies bound to heparin are detected.

DETAILED DESCRIPTION OF INVENTION

Heparin acts indirectly to impair blood coagulation by specifically binding antithrombin III (ATIII). Binding of heparin to ATIII accelerates the formation of antithrombin III-thrombin (TAT) complexes, which neutralize thrombin, a clotting factor. Applicants' invention is based on the discovery that anti-heparin antibodies inhibit the formation of heparin accelerated TAT complexes. Applicants have described anti-heparin antibodies that interfere with the anticoagulant site on heparin which specifically binds ATIII and, as a result, prevent formation of TAT complexes. As also described, Applicants carried out immunospecificity studies of anti-heparin antibodies in purified immunoglobulin obtained from individuals at risk for thrombosis, and identified sera containing high affinity anti-heparin antibodies which bind specifically to the pentasaccharide present in heparin, which binds antithrombin III. These antibodies have been shown to react with a disaccharide present in the heparin pentasaccharide.

Thus, Applicants' discovery has allowed the development of a method for the detection of anti-heparin antibodies in an individual indirectly or directly. In the method, the presence of anti-heparin antibodies which react with the heparin pentasaccharide which binds antithrombin III is determined. As used herein, the term anti-heparin antibodies refers to antibodies which bind heparin or heparan sulfate. Antibodies which bind heparin have been previously described in patients with heparin-induced thrombocytopenia, post-streptococcal glomerulonephritis and systemic lupus erythematosus (SLE). In patients with the anti-phospholipid antibody syndrome (APS), the presence of anti-phospholipid antibody is associated with morbid outcomes, particularly related to recurrent thrombosis. However, the cause of the thrombosis in these patients is unknown. Furthermore, the exact relationship between anti-phospholipid antibody as defined by the currently commercially available and clinically employed diagnostic test, and thrombosis is unclear. Applicants demonstrate herein that anti-phospholipid antibodies are particularly reactive with heparin.

As described in Example 2, APS affinity-purified IgG anti-heparin antibodies react with a disaccharide found in the specific heparin pentasaccharide that binds ATIII, resulting in inhibition of the heparin accelerated formation of TAT complexes. The disaccharide, termed UA-2S/GlcNS-6S, is found in residues IV and V of the heparin pentasaccharide and has the following structure:

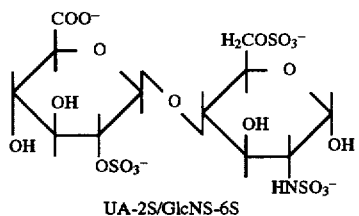

UA-2S/GlcNS-6S

In one embodiment, Applicants' method is one of indirectly detecting, in a sample obtained from an individual, the presence of anti-heparin antibodies which inhibit formation of the heparin accelerated antithrombin III-thrombin complex by detecting the presence of heparin accelerated antithrombin III-thrombin complex; the extent to which the complex occurred in the sample is indicative of (inversely related to) the extent to which anti-heparin antibodies are present in the sample (i.e., less complex is formed when anti-heparin antibodies are present than when they are not). In the indirect embodiment in which the presence of anti-heparin antibodies which inhibit formation of heparin accelerated antithrombin III-thrombin complex is detected, a sample to be assessed is combined with antithrombin III and heparin, thereby producing a first combination. The first combination is further combined with thrombin under conditions appropriate for formation of the heparin accelerated antithrombin III-thrombin complex, thereby producing a second combination. The extent to which the complex is formed in the presence of the sample is compared with the extent to which the complex is formed in the absence of the sample (the other conditions and reagents being the same). In one embodiment, the second combination is contacted with antibodies to thrombin which are present on (attached to) a surface. In this embodiment, the extent to which binding of the heparin accelerated antithrombin III-thrombin complex occurs in the presence of the sample is assessed and compared to the extent of binding which occurs in the absence of the sample by comparing the extent or amount of complex bound to the antibodies to thrombin on the surface. Formation of the complex to a lesser extent in the presence of the sample is indicative of the presence of anti-heparin antibodies in the sample. In the embodiment in which the second combination is contacted with antibodies to thrombin which are present on a surface, the presence of less complex on the surface (i.e., less antibody-bound complex) in the presence of sample than in its absence is indicative of the presence of anti-heparin antibodies in the sample.

The thrombin used in the assay method of the present invention can be captured using well known methods described in the art. For example, thrombin can be captured using surfaces such as beads, membranes, microtiter plates, and reagents such as polyclonal and monoclonal antibodies to thrombin and other thrombin-binding proteins.

Detection of the formation of heparin accelerated antithrombin III-thrombin complex can be done using methods well known to those skilled in the art. For example, thrombin can be detected using labelled streptavidin, alkaline phosphatase, peroxidase or using magnetic or fluorescent techniques. In addition, it requires no more than routine experimentation to capture ATIII in place of thrombin in the embodiment described above using methods well known to those skilled in the art. In this instance, for example, thrombin can be labeled (e.g., biotinylated) and detected (e.g. with streptavidin-alkaline phosphatase) to indicate the extent to which the heparin accelerated antithrombin III-thrombin complex is formed.

Further, it is possible that the reaction of the anti-heparin antibodies with heparin results in only partial interference with the binding of heparin to ATIII, with the result that the complex also includes immunoglobulin. One skilled in the art can determine ways of detecting the heparin-ATIII-immunoglobulin complex binding to thrombin using no more than routine experimentation. For example, polyclonal and monoclonal antibodies for detection of both ATIII and antibody (immunoglobulin), as well as bound heparin, can be produced by one skilled in the art. Detection methods such as radioisotope tagging, secondary antibodies, biotinylated antibody, iron, fluorescent and other labeled antibody can be used. In addition, detection of bound immunoglobulin can be performed using labelled protein A and G.

Finally, the signals which can be used to detect the complex in this embodiment of the invention include labelled streptavidin with alkaline phosphatases and peroxidases.

In another embodiment of the invention, a sample to be assessed is contacted with heparin present on a surface, and anti-heparin antibodies are detected directly. The methods for direct detection of anti-heparin antibodies include those well known to those skilled in the art. For example, methods for coating heparin on surfaces such as beads, membranes (e.g., nitrocellulose, immobilon-p) or microtiter plates can be used. For these methods, noncovalent methods, i.e. coating with protamine sulphate, polylysine or other proteins which may capture heparin or antibodies and other heparin-binding proteins can be used. In addition, heparin can be covalently attached to protein (e.g., biotin, bovine serum albumin (BSA) or keyhole limpet hemocyanin (KLH) and the heparin-protein complex can be bound to surfaces. All forms of heparin can be used in this embodiment, such as low molecular weight heparin and the heparin pentasaccharide. Detection of bound anti-heparin antibodies is determined using methods such as RIA, ELISA with protein A or protein G, or anti-immunoglobulin, followed by detection systems such as alkaline phosphatase, peroxidase or a radiolabelled substance.

The sample to be assessed by the method of the present invention can be any sample which contains immunoglobulins, such as IgG, IgA and IgM. For example, a blood (e.g., serum or plasma) or lymph sample can be used. A preferred sample is purified immunoglobulin, such as IgG, IgA, or IgM. Purification of the immunoglobulin from a sample can be performed by a variety of methods well known in the art. Serum immunoglobulin can be purified using conventional methods employing protein A, protein G, anti-IgM or anti-IgG affinity chromatography. Methods include, but are not limited to, column chromatography, capture in microliter plates, on nitrocellulose or other membranes, or through the use of coated or covalently linked beads, followed by centrifugation (for example, Sepharose® beads, dry styrene or magnetic beads). In addition, immunoglobulin can be purified on heparin directly by a variety of methods. The methods for purification of immunoglobulin on heparin directly are well known to those skilled in the art and include affinity column chromatography, microcentrifugation on heparin beads, e.g., magnetic beads.

In the indirect embodiment, the sample must contain (as obtained or as modified) heparin, antithrombin III and thrombin in appropriate concentrations for complex formation to occur. If the sample, as obtained, does not contain these components, one or all (i.e., heparin, antithrombin III, thrombin) can be added in appropriate amounts. In the direct embodiment, the sample is combined with heparin or with an antibody which binds the site on the anti-heparin antibody which recognizes the anticoagulant site on heparin (an anti idiotype antibody). In the former instance, all anti-heparin antibodies will be detected and, in the latter, anti-heparin antibodies specific for the anticoagulant site on heparin will be detected.

Applicants' invention can be used to detect anti-heparin antibodies in individuals, such as individuals in whom heparin activity is or appears to be compromised. For example, Applicants' invention can be used to detect anti-heparin antibodies in individuals treated with heparin in any form, and individuals with antiphospholipid antibody syndrome, SLE, thrombocytopenia or thrombosis, and other autoimmune diseases.

It is possible, based on Applicants' work, to provide a molecule which blocks the activity of anti-heparin antibodies and, thus, prevents the anti-heparin antibodies from interfering with formation of the heparin accelerated antithrombin III-thrombin complex (i.e., such a molecule inhibits anti-heparin antibodies). Such a molecule acts as a decoy or substitute for heparin in that it is bound specifically by anti-heparin antibodies. As a result, the anti-heparin antibodies are unavailable to bind heparin in an individual and heparin can exert its usual effects. A molecule such as the disaccharide U2-2S/GlcNS-6S can be used as a heparin decoy, which will be bound by the anti-heparin antibodies, thus rendering them unable to bind heparin. A heparin decoy can be administered to an individual in whom anti-heparin antibodies are present. Alternatively, blood removed from and returned to an individual, such as through dialysis, can be contacted with a heparin decoy, the resulting anti-heparin antibody-heparin decoy complex can be removed (e.g., filtered) from the blood and the blood can be returned to the individual.

The present invention is illustrated by the following examples, which are not intended to be limiting in any way.

EXAMPLES

Example 1

Detection of Anti-Heparin Antibodies in Patients with Systemic Lupus Erythematosus Methods and Materials Reagents DEAE-Sepharose® CL-6B gel filtration media, Sepharose® CL-4B gel filtration media, EAH-Sepharose® 4B gel filtration media and double-stranded DNA-cellulose were obtained from Pharmacia Fine Chemicals (Piscataway, N.J.). Heparan sulfate (HS) (sodium salt, derived from bovine kidney), chondroitin sulfate, hyaluronate, heparin, cardiolipin, herring sperm DNA, and goat anti-human IgG-coupled Sepharose® 4B gel filtration media were purchased from Sigma Chemical So. (St. Louis, Mo.). Phosphorylcholine was obtained from Avanti (Alabaster, Ala.). Biotinylated goat anti-human IgG and streptavidin-alkaline phosphatase were purchased from Jackson ImmunoResearch (West Grove, Pa.). A vascular endothelial cell line from murine aorta, MAE22106, was kindly provided by Dr. Robert Auerbach (University of Wisconsin, Madison, Wis.). (Obeso, J. et al., *Lab. Invest.* 63:259–269 (1990)).

Human Sera

Sera from normal controls and patients with SLE were obtained from the Department of Second Internal Medicine, Tohoku University School of Medicine, Sendai, Japan. All patients with SLE fulfilled the 1982 revised criteria (Tan, E. M. et al., *Arthritis Rheum.* 25:1271–1277 (1982). The disease was considered active when the patient had clinically identifiable symptoms in at least one organ, based on previously published criteria (Budman, D. R., et al., *Scand. J. Immunol.* 6:575–579 (1977)).

Preparation of IgG from human sera. Igs from human sera were initially purified on protein G. To further purify the IgG fraction, the Ig was extensively dialyzed against 0.01 mol/L phosphate buffered saline (PBS), pH 7.4, and applied to a goat-antihuman IgG-coupled Sepharose® 4B gel filtration media column (Sigma). Unbound proteins were washed off with PBS and the bound IgG was eluted with 0.1 mol/L glycine-HCl pH 2.7. The eluate was immediately neutralized with 1.0 mol/L TRIS-HCl pH 9.0 and extensively dialyzed against PBS. The concentration of dialyzed IgG solution was determined by capture enzyme-linked immunosorbent assay (ELISA) using commercially available human IgG (Sigma) as a standard sample.

Preparation of Affinity-Purified Human IgG

Preparation of heparan sulfate-EAH-Sepharose® 4B gel filtration media column. Twenty milligrams of heparan sulfate (HS) (Sigma) was placed in 10 ml of PBS and briefly sonicated until solubilized. A total of 2.5 ml of 250 mM benzoquinone in absolute ethanol was added to the HS solution and rotated in the dark at room temperature for one hour. A total of 100 ml of 95%. ethanol/0.1M sodium acetate (ethanol acetate) was added and the mixture was centrifuged at 12.000 g for 20 minutes. The pellet was retained and washed twice with ethanol acetate. Then 8 ml of 0.1M sodium bicarbonate, pH 8.5 (carbonate buffer), was added to the pellet. The solution was briefly sonicated and dialyzed overnight against 4 liters of carbonate buffer. The concentration of HS in the dialyzed solution, referred to as benzoquinone-HS, was determined by glucuronate analysis (Bitter, T. and Muir, H. M., *Anal. Biochem.* 4:330–335 (1962). One gram of EAH-Sepharose® 4B gel filtration media (Pharmacia) was washed and swollen in 10 ml of 0.1M sodium bicarbonate (pH 8.5)–25% ethanol. Two milligrams of benzoquinone-HS in 2 ml of carbonate buffer was added to the EAH-Sepharose® 4B gel filtration media solution and rotated overnight at 4° C. The gel was washed alternately with carbonate buffer and 0.1M sodium bicarbonate, pH 4.0, three times, equilibrated with PBS, and packed into the column. The coupling efficacy of benzoquinone-HS to the gel was >95%. The column was extensively washed with 4M guanidine-HCl/2M NaCl, pH 7.4, and reequilibrated with PBS prior to use.

Affinity purification of human IgG with HS-EAH-Sepharose® 4B gel filtration media. Twenty milligrams of purified serum IgG in PBS was applied to HS-EAH-Sepharose® 4B gel filtration media column. The column was washed with PBS and bound IgG was eluted with 4M guanidine-HCl/2M NaCl, pH 7.4. The eluted IgG was sequentially dialyzed against 500 ml of 2M guanidine-HCl/ 1M NaCl, 1M guanidine-HCl/0.5M NaCl, 0.5M guanidine-HCl/0.25M NaCl, and PBS. The concentration of affinity-purified IgG was determined by ELISA.

Affinity purification of human IgG with DNA cellulose. Human IgG was affinity-purified with DNA-cellulose using the methods described by Suenaga, R., et al., *J. Immunol. Methods* 93:131–140 (1986). Two grams of double-stranded DNA-cellulose (Pharmacia) was equilibrated with PBS and packed into a glass column. The DNA-cellulose column was extensively washed with 4M guanidine-HCl/2M NaCl, pH 7.4, until no leakage of DNA from the cellulose could be detected and reequilibrated with PBS. Twenty milligrams of purified serum IgG in PBS was applied to the column and allowed to pass through at a flow rate of 3 ml/hr at 4° C. The column was extensively washed with PBS and the bound IgG was eluted with 4M guanidine-HCl/2M NaCl, pH 7.4. The eluted IgG was sequentially dialyzed and the concentration was determined as described above.

Vascular Heparan Sulfate Proteoglycan Antigens

Native vHSPG and vHSPG protein core. Native vHSPG was purified from bovine glomeruli as previously described (Fillit, H., et al., *J. Exp. Med.* 161:277–289 (1985)). VHSPG protein core was also prepared as previously described employing chemical deglycosylation (Fillit, H., et al., *Autoimmunity* 14:243–249 (1993)).

Conjugation of heparan sulfate to BSA. Intact heparan sulfate was conjugated to BSA (Cohn fraction V, Sigma) to assure adsorption of HS to ELISA plates via protein portion of conjugate. Ten milligrams of HS was coupled to benzoquinone as described above. Twenty milligrams of BSA was added to the benzoquinone-HS in 10 ml of 0.1M sodium bicarbonate, pH 8.5, and rotated overnight at 4° C. The HS-conjugate BSA was then precipitated by the addition of saturated ammonium sulfate at 4° C. The mixture was centrifuged at 12,000 g for 20 minutes, and the pellet was resuspended in PBS. The solution was extensively dialyzed against PBS. The final solution, referred to as HS-BSA, contained 0.5 mg/ml of HS and 1 mg/ml of BSA, as estimated by protein BCA assay (Pierce, Rockford, Ill.) and glucuronate analysis (Bitter, T. and Muir, H. M., *Anal. Biochem.* 4:330–335 (1962). Biochemical modifications of HS for the study of the immunodominant site of anti-HS antibodies. To investigate the immunodominant site of HS, several biochemically modified HS antigens were prepared as follows (a) Carboxyl reduction (carbodiimide-HS): To specifically reduce negatively charged carboxyl groups (Taylor, R. L., and Conrad, H. E., *Biochemistry* 11:1383 (1972)), 10 mg of HS was dissolved in 3.3 mol of distilled water. A total of 63.9 mg of 1-ethyl-3-(3-dimethylaminopropyl) carbodiimide (EDAC) was slowly added, and the solution was titrated to pH 4.7. A total of 6.6 ml of 2M $NaBH_3$ was slowly added, with the pH maintained at 8.0 with 4N HCl. Then, the reaction mixture was magnetically stirred for 30 minutes. Finally, the material was dialyzed and lyophilized. (b) Desulfation (desulfated HS): To study the role of sulfate in antibody binding, desulfation was performed. Solvolysis (Kosakai, M. and Yosizawa, Z., *J. Biochem.* 86:147–153 (1979)) was employed to specifically eliminate 2-O-sulfate or 6-O-sulfate. For 2-O-desulfation, 5 mg of HS was dissolved in 5 ml of 0.1M HCl. The solution was heated to 100° C. for 70 minutes and then cooled to room temperature. The solution was neutralized with 0.1N NaOH and dialyzed against distilled water. The pH after dialysis was 5.1. The material was then lyophilized and stored at 4° C. For 6-O desulfation and N-desulfation, the pyridine salt of HS was created. Ten milligrams of HS was dissolved in 10 ml of distilled water and then dialyzed against 0.01M HCl at 4° C. A final dialysis was performed against deionized water. The pH of the final solution was 3.17. The solution was then neutralized with pyridine to pH 7.5 and lyophilized. For 6-O-desulfation, 5 mg of the pyridine salt of HS was placed into a glass test tube containing 5 ml of DMSO/2% pyridine (100 μl) and heated at 100° C. for 9 hours. The solution was then diluted 50:50 with deionized water and dialyzed against deionized water and lyophilized. For N-desulfation, 5 mg of the pyridine salt of HS described above was dissolved in 5 ml of DMSO containing 5% distilled water (v/v). The sample was heated to 50° C. for 1.5 hours, with vortexing every 15 minutes for 20 seconds. Finally, 5 ml of deionized water was added, and the material was dialyzed against distilled water and lyophilized. (c) Free radical treatment ($H_2O_2$-HS): To test the effects of free radicals on immunoreactivity, 2.8 mg of HS was dissolved in 1 ml of distilled water. A total of 0.22 ml of 30% $H_2O_2$ of 1000 ppm $FeCl_3$ was added to the solution. The mixture was magnetically stirred for 3 days at 4° C. and the final material was dialyzed and lyophilized.

To demonstrate that HS derivatives were altered, they were chromatographed on FPLC employing a Superose® 12 gel filtration media column equilibrated in 50 mM sodium acetate at a flow rate of 0.75 ml/minute. The column was monitored by an Alcian blue dot blot assay, and fractions were analyzed by uronic acid analysis. Treatment of the HS by all methods resulted in a shift of HS chromatographic profiles toward the total volume of the column.

Immunologic Methods

ELISA: (a) Direct binding assay. Microtiter plates (Nunc) were coated with various antigens at 5 μg/ml, including vHSPG, HS-BSA and DNA in PBS at 4° C. overnight. For coating of DNA, plates were precoated with 5 μg/ml of protamine sulfate for 1 hour at room temperature. Plates were then blocked with 3% BSA-PBS and incubated with human sera diluted at 1:100 or purified IgG for 2 hours at room temperature. After extensive washing, biotinylated goat anti-human IgG was added to the plates for an additional 60 minutes. Plates were then incubated with streptavidin-alkaline phosphatase for 60 minutes and p-nitrophenyl phosphate was added. After 30 minutes, $OD_{405\ nm}$ was measured in an ELISA microplate reader to determine the amount of bound enzyme. (b) Competitive inhibition assay: Pilot experiments were carried out to determine the concentration of human IgG giving 50% of maximal binding to antigen-coated microtiter plates. Antibodies at concentrations corresponding to 50% binding were preincubated with various amounts of inhibitors. Then the mixtures were transferred to antigen-coated plates and the binding was determined as above.

Cellular ELISA (CELISA) for anti-endothelial cell antibody. This assay was performed essentially using the method described by Heurkens, A. H. M., et al., *J. Immunol. Methods* 141:33–39 (1991). Murine vascular endothelial cell line MAE221067 was plated in flat-bottomed, 0.1% gelatin-precoated 96-well culture plates (Corning) at $2 \times 10^4$ cells/well. After 1–2 days, when the monolayer on the wells had reached confluent, the cells were fixed for 1 hour at 4° C. with 0.1% glutaraldehyde-PBS. After washing, the binding of human IgG was determined by ELISA as described above.

Immunospecificity studies by enzymatic alteration of antigens. To further investigate antigenic specificity, enzymatic digestions of plate fixed antigens were performed. Plate-fixed MAE, HS and DNA were incubated for 1 hour at 37° with 1 mU/50 liters of heparinase III (in 100 µg/ml $CaCl_2$, 100 µg/ml BSA, 0.1M Tris-buffered NaCl) or 10 U/50 liters of DNase I (in 5 mM $MgCl_2$, 100 µg/ml BSA, 0.1M sodium acetate, 0.05M NaCl). Binding of SLE affinity-purified antibody to HS, DNA, or MAE was then investigated as described above for ELISA studies.

ELISA for detection of SLE IgG inhibition of thrombin-antithrombin III complex formation. Human antithrombin III (ATIII) was a gift from Dr. D. Mache-Aronson (American National Red Cross Laboratories, Bethesda, Md.). The ATIII was biotinylated using D-biotinoylaminocaproic acid N-hydroxysuccinimide ester according to the manufacturer's directions (Boehringer-Mannheim). Human α-thrombin was generously provided by Dr. John Fenton (N.Y. State Department of Health, Albany, N.Y.). Rabbits were immunized intradermally with human thrombin to obtain anti-sera. The IgG fraction was isolated from the rabbit sera and affinity purified using immobilized thrombin.

The assay for detecting thrombin-antithrombin III (TAT) complexes accelerated by heparin was performed with modifications of the method detailed for ELISA of thrombin-antithrombin complexes (Harpel, P. C., and Fenton, J. W. L., *Ann. N. Y. Acad. Sci.* 485:184–198 (1986)) and our previously described methods (Shibata, S. et al., *Clin. Immunol. Immunopathol.* 67:264–272 (1993)). Microtiter plates (Nunc) were coated with 4 µg/ml of the IgG fraction of rabbit anti-human thrombin overnight at 4° C. and blocked with 3% BSA-PBS. Biotinylated ATIII, 0.5 µg/ml at final concentration, was preincubated with various amounts (0.01–0.5 µg/ml) of heparin for 15 minutes at 37° C. Purified human thrombin, 0.25 µg/ml at final concentration, was added to the mixture and incubated for 15 minutes at 37° C., and the reaction was terminated by the addition of 1 µg/ml D-phenylalanyl-L-prolyl-Larginine chloremethylketone (Calbiochem). The mixtures were transferred to rabbit anti-human thrombin-precoated wells and incubated for 1 hour at room temperature. The plates were then incubated with streptavidin-alkaline phosphatase and then with the substrate p-nitrophenyl phosphate. After 30 minutes, $OD_{405\ nm}$ was measured in an ELISA microplate reader to determine the amount of TAT complex formed in the assay. The amount of TAT complex increased proportionally to the dose of heparin preincubated with ATIII.

To examine whether SLE IgG antibody affected TAT complex formation by inhibiting the effect of heparin, various concentrations of SLE and control IgG were preincubated with the optimum amount of heparin (0.1 µg/ml) for 30 minutes at 37° C. and then for 30 minutes at 40C. Finally, the amount of TAT complex was determined as above.

Data analysis. Statistical analysis was performed using $X^2$ test.

RESULTS

Direct binding studies of human sera to DNA, HS, and vHSPG. Human sera from 15 normal controls and 14 patients with active SLE were investigated by ELISA for direct binding of IgG to DNA, vHSPG, and HS. The binding of normal sera to DNA, vHSPG, and HS was 0.072±0.029, 0.098±0.045, and 0.113±0.062, respectively (mean±SD of $OD_{405\ nm}$). The data were then analyzed by $X^2$ analysis, employing a cutoff value of one standard deviation beyond the mean for control sera. By this method, 13/14 active SLE sera were positive for anti-DNA antibody activity, while none of the controls were considered reactive. Similarly, 8/14 SLE sera were positive for anti-vHSPG antibody, and 6/14 SLE sera were positive for anti-HS antibody, while no control sera were considered positive in either of these assays. Thus, in active SLE sera, the antibody reactivity to vHSPG (P=0025), HS (P=0.0169), and DNA (P=0.0001) were significantly higher than normal sera.

Specificity of binding to HS of human affinity purified SLE total IgG. The fine specificity for HS of affinity-purified SLE total IgG from two SLE patients with active disease (biopsy proven glomerulonephritis, WHO classification type IV) was investigated by competitive immunoinhibition employing HS-BSA as an antigen. Liquid-phase competitive immunoinhibition studies demonstrated that HS and DNA were effective inhibitors of HS reactivity, while phospholipids (cardiolipin and phosphorylcholine) as well as other GAGs (including HA and chondroitin sulfate) were relatively poor inhibitors of HS reactivity. Heparin, a GAG related to HS, was the most effective inhibitor of HS reactivity.

Biochemical alterations of HS were used to investigate the role of specific epitopes in the immunodominant site of HS recognized by SLE IgG. 2-O-desulfation significantly reduced the antigenicity of HS. Carbodiimide treatment also reduced the antigenicity of HS. 6-O-desulfation and N-desulfation enhanced the antigenicity of HS, suggesting that these epitopes may not be critical to antibody binding or may hide antigenic epitopes. Free radical treatment of HS destroyed the antigenic site. Taken together, these data indicate that a uronic acid epitope containing carboxyl groups and 2-O-sulfate groups (found solely on uronic acids in GAGs) plays a major role in the immunodominant site of HS recognized by SLE IgG, and that nonspecific charge interactions due to the presence of sulfate do not solely account for the observed HS immunoreactivity.

Specificity of binding to DNA of human affinity-purified SLE total IgG. The fine specificity for DNA of affinity-purified SLE total IgG from two SLE patients with active disease was investigated by competitive immunoinhibition employing DNA as antigen. Native vHSPG and HS were equally effective inhibitors as DNA. While anti-DNA activity could be inhibited by HS, neither hyaluronic acid nor chondroitin sulfate was an effective inhibitor. Heparin was also an effective inhibitor of anti-DNA activity in this assay. Cardiolipin and phosphorylcholine were either poor or ineffective inhibitors of SLE IgG anti-DNA reactivity. These data demonstrate that SLE IgG anti-DNA antibody cross-react with vHSPG antigens, particularly HS, when employing DNA as antigen, and also cross-react with heparin.

Immunospecificity studies of SLE IgG further affinity-purified on DNA and HS. The IgG preparations obtained from two active lupus sera described above were further purified with DNA-cellulose or HS-EAH-Sepharose® 4B gel filtration media. As previously reported (Suenaga, R. et al., *J. Immunol. Methods* 93:131–140 (1986)), DNA-anti-DNA complexes were so stable than only a trace of IgG was eluted with 3M NaCl. Guanidine (4M guanidine-HCl/2M NaCl, pH 7.4) was required to elute the affinity-bound antibodies. The same elution buffer was used for the HS column because the binding of SLE IgG to HS-Sepharose® gel filtration media was also of equally high affinity. The amount of IgG in each fraction (total IgG loaded on the columns and eluted IgG) was determined by sandwich ELISA. From 20 mg of SLE 1 IgG applied to each column, 0.22 mg (1.1%) of anti-DNA IgG, and 0.06 mg (0.3%) of anti-HS IgG were recovered. Similarly, 0.18 mg (0.9%) and 0.08 mg (0.4%) of anti-DNA and anti-HS IgG respectively, were obtained from 20 mg of SLE 2 IgG applied to each column.

To investigate whether actual enrichment of binding activity resulted from antigen-specific affinity purification, direct binding assays to DNA, HS, and vHSPG were conducted employing purified total IgG and affinity-purified IgG. Affinity purification of SLE anti-DNA antibodies resulted in enhancement of anti-HS and anti-vHSPG reactivity. Similarly, affinity purification of anti-HS antibodies also resulted in enhancement of DNA, HS, and vHSPG reactivity. No enhancement of reactivity to bovine serum albumin was noted with SLE IgG. In addition, no affinity enhancement was noted for other antigens studied including type 1 collagen, actin, or other anionic antigens such as cardiolipin (phospholipid). In addition, IgG which did not bind to the HS and DNA affinity columns showed no binding to DNA, HSPG, or HS. Finally, no enhancement of reactivity was seen with affinity-purified normal IgG to any of the antigens studied.

Binding specificity of affinity-purified SLE IgG to murine aortic endothelial cells. To determine if affinity-purified SLE anti-HS IgG antibody from the two patients with active SLE bound to endothelial cells, binding of affinity-purified anti-DNA and anti-HS antibody to the surface of murine aortic endothelial cells (MAE) was studied. Significant concentration of MAE reactivity was noted in the affinity-purified fractions of antibody compared to whole IgG. To investigate the fine specificity of the immunodeterminants on MAE cell surface, liquid-phase competitive immunoinhibition studies of reactivity to MAE were performed employing affinity-purified anti-DNA and anti-HS IgG antibodies. Affinity-purified SLE IgG anti-HS antibody reactivity to MAE was inhibited by vHSPG, HS, heparin, and DNA but not by phospholipids (cardiolipin and phosphorylcholine). Similar findings were noted with affinity-purified anti-DNA antibody.

Since the binding of anti-DNA and anti-HS SLE IgG to MAE was significantly inhibited by DNA, the possibility that cell surface DNA accounted for the observed immunoreactivity was investigated. MAE were preincubated with DNase, and the reactivity of DNase-treated MAE was compared to untreated MAE. DNase treatment resulted in no change or some (10–20%) enhancement in immunoreactivity to MAE by SLE affinity-purified anti-DNA and anti-HS antibody. However, treatment of MAE with heparitinase reduced the reactivity of anti-DNA and anti-HS antibody by 30–50%. As a control for comparison, DNase treatment of plates coated with DNA reduced the reactivity of anti-DNA antibody by approximately 40%. Heparitinase treatment of HS-coated plates reduced the immunoreactivity of both anti-DNA and anti-HS antibody by 30–50%. Thus it is likely that incomplete enzymatic digestion by heparitinase accounts for the lack of 100% inhibition of antibody reactivity to MAE by heparitinase, suggesting that the anti-DNA and anti-HS antibody are reactive with cell surface HS antigen, and not DNA, on MAE.

SLE IgG inhibition of thrombin-antithrombin III complex formation. vHSPG plays an important role in the maintenance of normal anticoagulation at the endothelial cell surface via binding of antithrombin III (Mertens, G. et al., *J. Biol. Chem.* 267:20435–20443 (1992)). As noted above, SLE IgG are reactive with vHSPG. SLE IgG anti-DNA and anti-HS antibodies also bound heparin with high affinity and were reactive with HS at the endothelial cell surface. In order to investigate the functional significance of this binding interaction, we employed a modification of our previously described methods, (Shibata, S. et al., *Clin. Immunol. Immunopathol.* 67:264–272 (1993)) to investigate whether SLE IgG or affinity-purified SLE IgG anti-DNA and anti-HS antibody can inhibit the formation of thrombin-antithrombin III (TAT) complex formation and therefore promote a procoagulant state. Since anti-HS and anti-DNA antibodies cross-react with heparin, and since the anticoagulant pentasaccharide which binds antithrombin III is contained in less than 1% of the total GAG content of HS (Marcum, J. A., et al., *J. Biol. Chem.* 261:7507–7517 (1986)), but is present in heparin as a repeating unit in high concentration, we investigated the inhibition of TAT complex formation employing heparin as an accelerant.

The amount of TAT complex formed in the assay increased proportionally to the dose of heparin preincubated with ATIII. Using the optimum amount of heparin, the effect of normal and active SLE IgG on TAT complex formation was determined. A decrease in TAT complex formation was caused by SLE IgG in a dose-dependent fashion, while little or no decrease in TAT complex formation was caused by normal IgG. Although 2 mg/ml of total IgG was necessary to cause 100% inhibition of TAT complex formation, approximately 20 µg/ml of specific affinity-purified anti-heparin sulfate IgG was required for 50% inhibition. These data are consistent with the observation noted above that approximately 1% of the total IgG from SLE patients bound to the HS affinity column and contained anti-HS antibody activity.

Example 2

Detection of Anti-Heparin Antibodies in Patients with Antiphosphilipid Antibody Syndrome Materials and Methods Reagents Heparin, heparin disaccharides, heparinase (I and III), HS, cardiolipin, heparin-agarose, and goat-antihuman IgG-coupled Sepharose® 4B gel filtration media were purchased from Sigma Chemical Co. (St. Louis, Mo.). Biotinylated goat-antihuman IgG and streptavidine-alkaline phosphatase were purchased from Jackson ImmunoResearch (West Grove, Pa.). Cardiolipin cofactor (β-2-microglobulin) was purified by previously described methods. (Gharavi, A. E., et al., *J. Clin. Invest.* 90:1105 (1992)).

Human subjects

Sera from patients and controls were obtained from the division of Rheumatology, Department of Medicine, Hospital for Special Surgery (Dr. Gharavi) and from the Coagulation Laboratory, Division of Hematology, Mount Sinai Hospital, New York, N.Y. All patients with APS fulfilled the major criteria for the disease. (Lockshin, M. D., *Curr. Opin. Rheum.* 3:797 (1991)).

Two cases of APS were studied in depth. Patient 1 was a 58-year-old white man who was admitted with increased lethargy and right-flank pain. The past medical history was significant for a progressive dementia of 1-year's duration, peripheral neuropathy, and retinal artery occlusion 4 months before admission, at which time the patient was found to have elevated IgG anticardiolipin antibodies (greater than 143 ACA GPL units; normal is less than 23). There were no IgM anticardiolipin antibodies. He was treated with warfarin. On admission, a chest x-ray showed a right lower lobe infiltrate with congestive heart failure. An electrocardiogram showed a new right bundle branch block pattern with a left-anterior hemiblock and an old inferior wall myocardial infarction. A head computed tomograph showed marked cerebral atrophy for the patient's age and an old right temporal-occipital infarct. Laboratory studies showed a negative ANA, anti-ds DNA antibody. Venereal Disease Research Laboratory (VDRL), and cryoglobulins. The platelet count was 95,000/mm$^3$; bone marrow showed normal megakaryocytes. The activated partial thromboplastin time (APTT) was 64.6 seconds (control=34.1 seconds; reference range=25.0 to 33.0 seconds) and prothrombin time was 21.6 seconds (control=10.9 seconds; reference ranges=11.0 to 13.2 seconds). Mixing studies showed the presence of an inhibitor. The bleeding time was 8.5 minutes. Anticardiolipin IgG titers were above 143 ACA GPL units (normal range is less than 23); IgM ACA was within normal limits. Two days after admission the patient became increasing dyspneic and hypertensive while on anticoagulant therapy. Ventilation/perfusion lung scanning showed a pulmonary embolism. He was placed on intravenous heparin, but despite large doses of heparin (up to 2,000 U/hr), the APTT remained just at or below therapeutic range, and he required a Greenfield filter. The patient then developed two subendocardial myocardial infarctions despite continued anticoagulation. His mental status deteriorated and he went into a coma. He required steroids because of bilateral adrenal hemorrhages and adrenal insufficiency. Because of his deteriorated condition despite therapy, the patient was treated with a course of plasmapheresis. After a long and complicated course, he recovered completely with continued plasmapheresis and intravenous heparin. He was discharged 4 months after admission and given Coumadin and aspirin.

Patient 2 was a 41-year-old woman of Peruvian origin who presented to clinic for evaluation of spontaneous bruisability that had developed over the preceding 6 months. Her history was significant for a right-lower extremity deep vein thrombosis that had been treated with anticoagulant therapy 15 years before. The obstetrical history was significant for two normal pregnancies, followed by four sequential miscarriages. The patient was known to have a biologic false positive VDRL. On examination the patient had multiple, scattered 1-cm ecchymoses in her upper and lower extremities with some of the ecchymosis having central raised tender nodules. Her laboratory studies were significant for a hematocrit 32.1%, platelets 124,000, positive Coombs test that showed IgG, IgA, IgM, C3D, and C4 on her red blood cells, along with a positive Ham's test with 10.5% hemolysis, antiplatelet antibodies were negative. Coagulation screening studies showed prothrombin time of 14.9/11.7 seconds (reference range=11.0 to 13.2 seconds), APTT of 43.1/30.1 seconds (reference range=25.0 to 33.0 seconds), anticardiolipin IgG antibody titer=54.0 ACA GPL units (normal<23), anticardiolipin IgM titers were within normal limits. Additional studies showed a manual APTT of 104.0/52 seconds. Mixing studies were positive for a circulating lupus anticoagulant. The patient was diagnosed as having SLE with the antibospholipid syndrome.

Preparation of IgG from human sera. Igs from human sera were initially purified on protein G. To further purify the IgG fraction, the Ig was extensively dialyzed against 0.01 mol/L phosphate buffered saline (PBS), pH 7.4, and applied to a goat-antihuman IgG-coupled Sepharose® 4B gel filtration media column (Sigma). Unbound proteins were washed off with PBS and the bound IgG was eluted with 0.1 mol/L glycine-HCl pH 2.7. The eluate was immediately neutralized with 1.0 mol/L TRIS-HCl pH 9.0 and extensively dialyzed against PBS. The concentration of dialyzed IgG solution was determined by capture enzyme-linked immunosorbent assay (ELISA) using commercially available human IgG (Sigma) as a standard sample.

Affinity purification of human IgG with heparin-agarose. A 5-mL column of heparin-agarose was equilibrated with PBS. Purified serum IgG in PBS was loaded on the column, the fall through collected, and the column was washed with 20 mL PBS. Two ml fractions were collected. Bound IgG was eluted stepwise with 20 mL each of 0.3 mol/L, 0.6 mol/L, 1 mol/L NaCl and 4 mol/L guanidine HCl/2 mol/L NaCl, pH 7.4. The column was monitored by spectrophotometry at 280 nm. Unbound material in the fall-through and the wash were pooled and rechromatographed. Peak fractions from the first chromatography were pooled and dialyzed against PBS, and the concentration of IgG in the dialyzed material was determined by capture ELISA. This peak fraction IgG was used for further immunologic studies.

Conjugation of HS to bovine serum albumin (BSA). Intact HS was conjugated to BSA (Cohn fraction V) to assure adsorption of HS to the radioimmunoassay plates via protein portion of the conjugate. Twenty milligrams of HS were placed in 10 mL PBS and briefly sonicated until solubilized. Two and a half milliliters of 250 mmol/L benzoquinone in absolute ethanol were added to the HS solution and rotated in the dark at room temperature for 1 hour. Of 95% ethanol/0.1 mol/L sodium acetate (100 mL) was added, and the mixture was centrifuged at 12,100 g for 20 minutes. The pellet was retained and washed twice with ethanol acetate. Then 10 mL of PBS was added to the pellet. The solution was briefly sonicated and dialyzed overnight against 4 L of PBS. 16 mg of BSA was added to the solution and rotated overnight at 4° C. The HS-BSA conjugate was then precipitated by the addition of 90 mL of saturated ammonium sulfate at 4° C. The mixture was then centrifuged at 12,100 g for 20 minutes, and the pellet was resuspended in PBS. The solution was again dialyzed against PBS. The final solution, referred to as HS-BSA, contained 15 mg/mL of BSA and 16 mg/mL of HS, as estimated by protein BCA assay (Pierce, Rockford, Ill.) and glucuronate analysis respectively. (Bitter, T. and Muir, H. M., Anal. Biochem. 4:330–335 (1962).

Digestion of heparin with heparinase I and III. Heparinase digestions (3 milliunits/mg heparin) were performed in 0.1 mol/L TRIS-HCl, pH 7.2 containing 5 mmol/L calcium acetate in the presence of protease inhibitors (10 mmol/L N-ethylmaleimide, 1 mmol/L phenylmethanesulfonyl fluoride, and 0.035 mmol/L pepstatis A) for 1 hour with rotation. Subsequently, the mixture was heated at 90° C. for 30 minutes to denature the enzyme. Then the sample was centrifuged and the supernatant was recovered for use in inhibition experiments. The relative completeness of the heparinase digestions was evaluated by gel chromatography on Biogel P6 in PBS by modifications of standard methods. (Gallagher, J. T., et al., Int. J. Biochem 24:553 (1992)). The elutions from the column were monitored at 230 nm for digestion products and compared with the chromatographic profile of undigested heparin and the standard heparin disaccharides also used for inhibition studies. The results showed that heparinase I digested the majority of the material to small oligosaccharides (with a degree of polymerization <6 monosaccharides). Heparinase III resulted in slightly larger oligosaccharides (degree of polymerization >10 monosaccharides). To calculate molar compositions of the intact heparin and the heparinase digested materials used for immunoinhibition experiments, an estimated mean molecular weight of the intact heparin preparation was used (30 kD).

ELISA

Detection of antiheparin and anti-HS antibodies: Direct binding assay. For detection of anti-HS antibodies, plates were coated with HS-BSA (10 μg HS/mL in 0.1 mol/L sodium carbonate, pH 9.8) overnight at 4° C. For detection of anti-heparin antibodies, microtiter plates (Nunc, Roskilde, Denmark) were coated with 10 μg/mL of protamine sulfate in 0.1 mol/L sodium carbonate, pH 9.8, for 1 hour at room temperature. After coating, protamine sulfate-coated plates were washed in PBS-0.1% Brij (PBSB) and then incubated with 10 μg/mL of heparin overnight at 4° C. All plates were then blocked with 3% BSA-PBS, washed with PBSB and incubated with 50 μL purified human IgG from patients or controls diluted 1:1 in 50 μL 3% BSA-PBS for 2 hours at room temperature. After extensive washing, biotinylated goat-antihuman IgG in PBSB was added to the plates for further 60 minutes. Plates were then incubated with streptavidin-alkaline phosphatase in PBSB for 60 minutes, and p-nitrophenyl phosphate was added. After 30 minutes optical density (OD) at 405 nm was measured in an ELISA microplate reader to determine the amount of bound enzyme.

Detection of antiheparin and anti-HS antibodies: Competitive inhibition assay. Pilot experiments were performed to determine the concentration of human IgG giving 50% of maximal binding to antigen-coated microtiter plates. Antibodies (50 μL) at concentrations corresponding to 50% binding were preincubated with various amounts of inhibitors (50 μL) in PBSB. For inhibitions with cardiolipin/β-2-glycoprotein cofactor, 1 mL of cofactor containing 0.100 $OD_{280}$ U was added to 1 mL of a 100 μg/mL solution of cardiolipin and the mixture was used for inhibition. (Gharavi, A. E., et al., *J. Clin. Invest.* 90:1105 (1992)). All inhibition mixtures were then transferred to antigen-coated plates and the binding was determined as above.

Detection of anticardiolipin antibodies. These studies were performed essentially as previously described. (Gharavi, A. E., et al., *Ann. Rheum. Dis.* 46:1 (1987)).

Microtiter plates were coated with 50 μg/mL of cardiolipin in absolute ethanol and dried up overnight at 4° C. Plates were blocked with 10% heat inactivated fetal bovine serum (FBS)-PBS and incubated with human IgG diluted with 10% FBS-PBS for 2 hours at 4° C. Then the binding of IgG was determined as above.

ELISA for detection of human IgG inhibition of thrombin-anti-thrombin III complex formation. Human anti-thrombin III (ATIII) was a gift from Dr. D. Menache-Aronson (American National Red Cross Laboratories, Bethesda, Md.). The ATIII was biotinylated using D-biotinoylaminocaproic acid N-hydroxysuccinimide ester according to the manufacturer's directions (Boehringer-Mannheim, Indianapolis, Ind.). Human α-thrombin was generously provided by Dr. John Fenton (N.Y. State Department of Health, Albany, N.Y.). Rabbits were immunized intradermally with human thrombin to obtain anti-sera. The IgG fraction was isolated from the rabbit sera and affinity purified using immobilized thrombin.

The assay for detecting TAT complexes accelerated by heparin was performed with modifications of the method detailed for ELISA of thrombin-antithrombin complexes (Harpel, P. C., and Fenton, J. W. I., *Ann. N.Y. Acad. Sci.* 485:184 (1986)) and our previously described methods. (Shibata, S. et al., *Clin. Immunol. Immunopathol.* 67:264–272 (1993)). Microtiter plates (Nunc) were coated with 4 μg/mL of the IgG fraction of rabbit antihuman thrombin overnight at 4° C. and blocked with 3%. BSA-PBS. Biotinylated ATIII, 0.5 μ/mL at final concentration, was preincubated with various amounts (0.01 to 0.5 μg/mL) of heparin for 15 minutes at 37° C. Purified human thrombin, 0.25 μg/mL at final concentration, was added to the mixture and incubated for 15 minutes at 37° C., and the reaction was terminated by the addition of 1 μg/mL D-phenylalanyl-L-prolyl-L-arginine chloromethylketone (Calbiochem Inc., San Diego, Calif.). The mixtures were transferred to rabbit antihuman thrombin precoated wells and incubated for 1 hour at room temperature. The plates were then incubated with streptavidin-alkaline phosphatase and then with the substrate p-nitrophenyl phosphate. After 30 minutes, $OD_{405\ nm}$ was measured in an ELISA microplate reader to determine the amount of TAT complex formed in the assay. The amount of TAT complex increased proportionally to the dose of heparin preincubated with ATIII.

To examine whether human IgG antibody affected TAT complex formation by inhibiting the effect of heparin, 50 μL of various concentrations of APS and control IgG diluted in 3% BSA-PBS were preincubated with 50 μL of the optimum amount of heparin (0.1 μg/mL) for 30 minutes at 37° C. and then for 30 minutes at 4° C. Finally, the amount of TAT complex was determined as above.

Data Analysis. Statistical analysis was performed using the chi-square test.

RESULTS

Direct Binding studies of human IgG to cardiolipin, HS, and heparin. Human IgG (30 μg/mL) purified from the sera of five normal controls and seven patients with APS were investigated by ELISA for direct binding to cardiolipin, HS, and heparin. The binding of normal serum IgG to cardiolipin, HS, and heparin was 0.201±0.117, 0.264±0.037, and 0226±0.078, respectively (mean±SD of $OD_{405\ nm}$). The data were then analyzed by chi-square analysis, using cut-off values that were two standard deviations beyond the mean for control samples. By this method, 6/7, 5/7 and 7/7 APS IgG were positive for anticardiolipin, anti-HS, and antiheparin antibody activity, respectively. The IgG antibody activity to cardiolipin (P=0.019), HS (P=0.06) and heparin (P=0.004) were significantly higher in APS patients than in normal controls.

Purified IgG from two APS patients with high binding to heparin and cardiolipin and two normal controls were chosen for further investigation. Direct binding of purified serum IgG from these two APS patients to cardiolipin, HS, and heparin showed the dose-dependent nature of the reactivity to these molecules.

Affinity Purification of human IgG with heparin-agarose. Elution profiles of patient and control IgG samples were monitored by OD at 280 nm. Increasing concentrations (up to 3N) of NaCl, and 0.1 mol/L glycine, pH 2.3 failed to elute the APS antiheparin antibody, essentially eliminating the possibility that low-affinity electrostatic interactions alone account for the binding of APS IgG to the heparin column. Only 4 mol/L guanidine HCl/2 mol/L NaCl eluted the affinity bound IgG, indicating that the binding affinity of APS IgG to heparin was very high. The peak fractions of the initial guanidine buffer elutions from the two APS patient IgG samples were pooled and dialyzed against PBS, and the amount of IgG eluted from the heparin agarose determined to be 20 μg/mL and 6 μg/mL respectively. These samples were used below for further immunologic studies. No peak was seen in the guanidine elution profiles of the normal controls.

To estimate the percent of the loaded total IgG that bound the heparin agarose, all fractions in each of the stepwise elutions (except the peak fractions of the guanidine elutions described above) were pooled, dialyzed against PBS, and tested for IgG concentration. For the APS patients, these data were combined with the data obtained for the guanidine elution peak fractions. When 10 mg of purified APS IgG from two patients was applied to a 5-mL heparin agarose column, 0.19 mg (1.9%) and 0.17 mg (1.7%) of IgG was eluted with 4 mol/L guanidine/2 mol/L NaCl. Relative to the APS patients, only small quantities of IgG (0.05 mg or 0.5%) from normal controls were found in the pooled guanidine elutions from the heparin column.

APS affinity-purified IgG antiheparin antibody reacted with cardiolipin, HS, and heparin in a dose-dependent fashion. The reactivity of the affinity-purified antiheparin IgG to heparin was significantly enriched compared with that of total IgG. For example, the binding to heparin of patient 1 and patient 2 antiheparin IgG (1 μ/mL) was 1.001±0.069 and 1.069±0.171, respectively (mean±SD of $OD_{405\ nm}$), whereas the binding of total IgG fractions from the same patients at the same concentration was 0.276±0.014 and 0.225±0.014, respectively. Although the degree of enrichment was clearly not as great, binding enrichment of APS affinity-purified antiheparin IgG compared with the total IgG fraction was also noted in reactivity to cardiolipin and HS. This result would be expected because heparin is the homologous antigen used in the affinity purification procedure. These results show the presence of anticardiolipin reactivity and anti-HS reactivity in the APS affinity-purified IgG antiheparin antibody fraction.

Fine immunospecificity of affinity-purified antiheparin antibodies obtained from patients with APS. To investigate the immunologic specificities of the affinity-purified APS antiheparin antibodies, liquid-phase competitive inhibition studies were preformed using heparin as antigen. Affinity-purified APS antiheparin antibody was inhibited by HS, cardiolipin with cofactor, (Gharavi, A. E., et al., *J. Clin. Invest.* 90:1105 (1992)) and heparin. Cardiolipin alone had little effect. To further characterize the immuno-dominant epitope recognized by these antibodies, heparinase I or III was used to digest sulfated and nonsulfated regions of heparin, respectively. (Gallagher, J. T., et al., *Int. J. Biochem* 24:553 (1992)). Digestion of nonsulfated regions of heparin by heparinase III increased the antigenicity of the heparin preparations, whereas digestion of the highly sulfated regions of heparin by heparinase I reduced the antigenicity of heparin as recognized by APS affinity-purified antiheparin IgG.

Use of heparin disaccharides confirmed that specific sulfate residues were necessary for APS IgG antiheparin antibody recognition. The disaccharide α-ΔUA-2S-[1→4]-GlcNS-6S was the most effective inhibitor, almost equivalent to the intact heparin chain. Of interest, this same disaccharide is present in residues IV and V of the specific heparin pentasaccharide sequence that binds ATIII with high affinity. (Lindahl, U., and Kjellan, L., *Thromb. Haemost.* 66:44 (1991)). The disaccharides α-ΔUA-2S-[1→4]-GlcNS-6S and α-ΔUA-2S-[1→4]-GlcNS were poor inhibitors. Other data showed that disaccharides containing N-acetylated disaccharides, α-ΔUA-2S-[1→4]-GlcNAc and α-ΔUA-2S-[1→4]-GlcNAc-6S, were completely ineffective inhibitors of APS IgG anti-heparin antibody, further showing the specificity of APS IgG antiheparin antibody for the α-ΔUA-2S-[1→4]-GlcNS-6S disaccharide.

Inhibition of heparin-accelerated thrombin-antithrombin complex formation by APS IgG. We used a modification of our previously described methods (Shibata, S. et al., *Clin. Immunol. Immunopathol.* 67:264–272 (1993)) to investigate whether APS IgG antiheparin antibody can inhibit the heparin accelerated formation of TAT complex formation, and therefore, promote a procoagulant state. The addition of APS total IgG resulted in a dose-dependent inhibition of heparin-accelerated TAT complex formation. This inhibition was increased approximately 100-fold by APS affinity-purified antiheparin IgG. Essentially no inhibition of TAT complex formation was caused by normal IgG (up to 2 mg/mL). Approximately 5 μg/mL of APS affinity-purified antiheparin IgG was necessary to inhibit 50% of TAT complex formation, which is similar to the concentration of procoagulant antibody activity found in SLE sera containing lupus anticoagulants. (Gharavi, A. E., et al., *Ann. Rheum. Dis.* 46:1 (1987)).

Equivalents

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of detecting, in a sample obtained from a human, anti-heparin antibodies which inhibit formation of a heparin accelerated antithrombin III-thrombin complex, comprising:

providing a test measurement by
   a) reacting the sample with known amounts of heparin and antithrombin III to form a first complex comprising said heparin and said antithrombin III and, if anti-heparin antibodies which inhibit formation of the heparin accelerated antithrombin III-thrombin complex are present in the sample, a complex between the anti-heparin antibodies and said heparin;
   b) reacting the first complex with a known amount of thrombin to form the heparin accelerated antithrombin III-thrombin complex;
   c) measuring the amount of heparin accelerated antithrombin III-thrombin complex formed;
   providing a reference measurement by performing steps a)–c) in the absence of the sample and comparing the test measurement with the reference measurement, wherein the presence of the anti-heparin antibodies which inhibit formation of the heparin accelerated antithrombin III-thrombin complex in the sample is detected when the test measurement is lower than the reference measurement.

2. The method of claim 1 wherein the known amount of heparin is provided as a known amount of heparin pentasaccharide.

3. The method of claim 1 wherein the known amount of heparin is provided as a known amount of disaccharide UA-2S/GlcNS-6S.

4. The method of claim 1 wherein the sample is selected from the group consisting of blood, serum, lymph and saliva.

5. The method of claim 4 wherein the sample is serum.

6. Amended) The method of claim 1 wherein the sample is purified immunoglobulin.

7. The method of claim 6 wherein the purified immunoglobulin is selected from the group consisting of IgG, IgA and IgM.

8. The method of claim 1 wherein the sample in step a) is pre-incubated with said heparin before antithrombin III is added.

9. A method of detecting, in a sample obtained from a human, the presence of anti-heparin antibodies which inhibit the formation of a heparin accelerated antithrombin III-thrombin complex, comprising the steps of:

providing a test measurement by
- a) reacting the sample with known amounts of heparin and antithrombin III to form a first complex comprising said heparin and said antithrombin III and, if anti-heparin antibodies which inhibit formation of the heparin accelerated antithrombin III-thrombin complex are present in the sample, a complex between the anti-heparin antibodies and said heparin;
- b) reacting the first complex with a known amount of thrombin to form the heparin accelerated antithrombin III-thrombin complex;
- c) contacting the heparin accelerated antithrombin III-thrombin complex with a capture antibody immobilized on a solid surface, wherein the capture antibody binds to the heparin accelerated antithrombin III-thrombin complex or to a member thereof;
- d) measuring the amount of complex bound to the solid surface;

providing a reference measurement by performing steps a)–d) in the absence of the sample and comparing the test measurement with the reference measurement, wherein the presence of the anti-heparin antibodies which inhibit formation of the heparin accelerated antithrombin III-thrombin complex in the sample is detected when the test measurement is lower than the reference measurement.

10. The method of claim 9 wherein in step (c), the antibody attached to the surface is a thrombin-binding antibody.

11. The method of claim 9 wherein in step (c), the antibody attached to the surface is an antithrombin III-binding antibody.

12. The method of claim 9 wherein the known amount of heparin is provided as a known amount of heparin pentasaccharide.

13. The method of claim 9 wherein the known amount of heparin is provided as a known amount of disaccharide U-2S/GlcNS-6S.

14. The method of claim 9 wherein the sample is purified immunoglobulin.

15. The method of claim 14 wherein the purified immunoglobulin is selected from the group consisting of IgG, IgA and IgM.

16. The method of claim 9 wherein the sample in step a) is pre-incubated with said heparin before antithrombin III is added.

17. The method of claim 9 wherein the sample is selected from the group consisting of blood, serum, lymph and saliva.

18. The method of claim 17 wherein the sample is serum.

19. A method of screening for Systemic Lupus Erythematosus in a human, comprising;
- a) obtaining a test sample from the human;
- b) measuring in the test sample the quantity of anti-heparin antibodies which inhibit formation of a heparin accelerated antithrombin III-thrombin complex;
- c) measuring in a reference sample obtained from a human without Systemic Lupus Erythenatosus the quantity of said anti-heparin antibodies which inhibit the formation of the heparin accelerated antithrombin III-thrombin complex present; and
- d) comparing the quantity of said anti-heparin antibodies which inhibit the formation of the heparin accelerated antithrombin III-thrombin complex present in the test sample and in the reference sample, wherein a greater quantity of antiheparin antibodies which inhibit the formation of the heparin accelerated antithrombin III-thrombin complex in the test sample than in the reference sample indicates a positive screen for Systemic Lupus Erythematosus.

20. A method of screening for Antiphospholipid Antibody Syndrome in a human, comprising:
- a) obtaining a test sample from the human;
- b) measuring in the test sample the quantity of anti-heparin antibodies which bind heparin pentasacaharide;
- c) measuring in a reference sample obtained from a human without Antiphospholipid Antibody Syndrome the quantity of said anti heparin antibodies which bind the heparin pentasaccharide; and
- d) comparing the quantity of said antiheparin antibodies which bind the heparin pentasaccharide present in the test sample and in the reference sample, wherein a greater quantity of said antiheparin antibodies which bind the heparin pentasaccharide in the test sample than in the reference sample indicates a positive screen for Antiphospholipid Antibody Syndrome.

* * * * *